United States Patent [19]

Peter et al.

[11] 4,035,380
[45] July 12, 1977

[54] CERTAIN BENZAZOL-2-YLTHIO COMPOUNDS

[75] Inventors: Richard Peter; Walter Jenny, both of Basel, Switzerland

[73] Assignee: Ciba-Geigy AG, Basel, Switzerland

[21] Appl. No.: 54,849

[22] Filed: July 14, 1970

Related U.S. Application Data

[63] Continuation-in-part of Ser. No. 662,313, Aug. 22, 1967, abandoned.

[30] Foreign Application Priority Data

Aug. 29, 1966  Switzerland ............... 12485/66

[51] Int. Cl.² .................................. C07D 277/74
[52] U.S. Cl. .................... 260/306.6 R; 260/37 R; 260/40 R; 260/240 J; 260/256.5 R; 260/288 R; 260/302 S; 260/306.7 R; 260/307 D; 260/308 R; 260/309; 260/309.2; 260/465 D; 260/465 F; 260/477; 260/488 CD; 260/577
[58] Field of Search ............... 260/306.6 R, 240 J, 260/307 D, 309.2

[56] References Cited

U.S. PATENT DOCUMENTS

| 2,120,401 | 6/1938 | Felix et al. ............... 260/306.6 |
| 3,635,957 | 1/1972 | Genta ....................... 260/306.7 |

*Primary Examiner*—R. Gallagher
*Attorney, Agent, or Firm*—Karl F. Jorda; Edward McC. Roberts; Prabodh I. Almaula

[57] ABSTRACT

Water-insoluble styryl dyestuffs of the formula

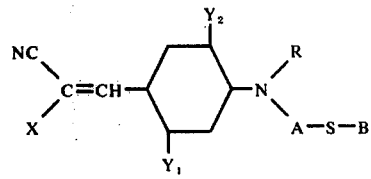

in which X represents a cyano, carbo-lower alkoxy or phenylsulphone group, $Y_1$ and $Y_2$ each represents a hydrogen atom, an lower alkyl or lower alkoxy or phenoxy group, R represents a lower alkyl, phenyl-lower-alkyl, cyano-lower-alkyl, lower alkoxyalkyl or acyloxyalkyl group or a radical of the formula —A—S—B, and A represent a lower alkylene group that may be substituted by a lower alkanoyloxy or a benzoyloxy group and B represents a heterocyclic radical.

4 Claims, No Drawings

CERTAIN BENZAZOL-2-YLTHIO COMPOUNDS

CROSS-REFERENCE TO RELATED APPLICATIONS

This application is a continuation-in-part of application Ser. No. 662,313, filed Aug. 22, 1967, now abandoned.

The present invention is based on the observation that new and valuable water-insoluble styryl dyestuffs of the formula

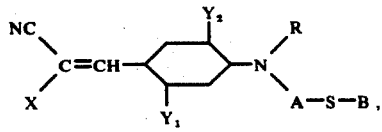

(1)

in which X represents a cyano, carbalkoxy or arylsulphonyl group, $Y_1$ and $Y_2$ each represents a hydrogen atom, an alkyl or alkoxy or phenoxy group, R represents an alkyl, phenalkyl, cyanoalkyl, alkoxyalkyl or acyloxyalkyl group or a residue of the formula —A—S—B, A represents an alkylene group which may be substituted and B represents an aryl, aralkyl or heterocyclic residue, can be obtained when (a) an aldehyde of the formula

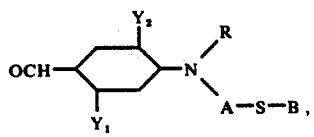

(2)

or an aldimine thereof is condensed with a compound of the formula

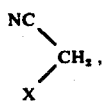

or (b) a styryl compound of the formula

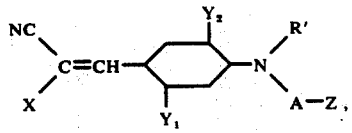

(3)

in which R' represents an alkyl, phenalkyl, cyanoalkyl, alkoxyalkyl or acyloxyalkyl group or a residue —A—Z, Z representing a halogen atom, and A, X, $Y_1$ and $Y_2$ have the meanings given above, is condensed with an aryl, aralkyl or heterocyclic mercaptan.

The compounds of the formula (2) which are used as starting materials may be obtained by condensing an arylmercaptoalkylaniline or an aralkylmercaptoalkylaniline of the formula

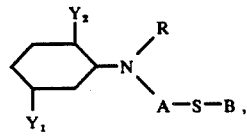

(4)

in which R, A, $Y_1$, $Y_2$ and B have the meanings given above, with dimethylformamide and phosphorus oxychloride according to Vilsmeyer and hydrolysing the intermediate product thus obtained.

Compounds that are particularly useful as starting materials for the process of the invention are aldehydes of the formula

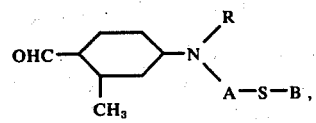

(5)

in which A, B and R have the meanings given above, and especially those of the formula

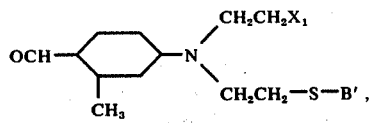

(6)

in which B' represents a phenyl or benzthiazolyl residue which may be substituted by halogen atoms or alkyl or alkoxy groups and $X_1$ represents a hydrogen atom or the residue —S—B'.

Examples are as follows: 2-methyl-4-N-methyl-N-phenylmercaptoethylaminobenzaldehyde, 2-methyl-4-N-ethyl-N-phenylmercaptoethylaminobenzaldehyde, 2-methyl-4-N-ethyl-N-para-chlorophenylmercaptoethylaminobenzaldehyde, 2-methyl-4-N-ethyl-N-(2',5'-dichlorophenyl-mercaptoethylaminobenzaldehyde, 2-methyl-4-N-ethyl-N-(2',4'-dichlorophenyl-mercaptoethylaminobenzaldehyde, 2-methyl-4-N-ethyl-N-para-methylphenylmercaptoethylaminobenzaldehyde, 2-methyl-4-N-ethyl-N-(2',5'-dimethylphenyl-mercaptoethylaminobenzaldehyde, 2-methyl-4-N-ethyl-N-ortho-methoxyphenylmercaptoethylaminobenzaldehyde, 2-methyl-4-N-ethyl-N-(2',5'-dimethoxyphenyl)-mercaptoethylaminobenzaldehyde, 2-methyl-4-N-ethyl-N-ortho-nitrophenylmercaptoethylaminobenzaldehyde, 2-methyl-4-N-ethyl-N-para-nitrophenylmercaptoethylaminobenzaldehyde, 2-methyl-4-N-ethyl-N-ortho-carbomethoxyphenylmercaptoethylaminobenzaldehyde, 2-methyl-4-N-ethyl-N-para-carbethoxyphenylmercaptoethylaminobenzaldehyde, 2-methyl-4-N-cyanoethyl-N-phenylmercaptoethylaminobenzaldehyde, 2-methyl-4-N-methoxyethyl-N-phenylmercaptoethylaminobenzaldehyde, 2-methyl-4-N-acetoxyethyl-N-phenylmercaptoethylaminobenzaldehyde, 2-methyl-4-N-benzyl-N-phenylmercaptoethylaminobenzaldehyde, 2-methyl-4-N-β-phenylethyl-N-phenylmercaptoethylaminobenzaldehyde, 2-methyl-4-N-ethyl-N-phenylmercaptoethylaminobenzaldehyde, 2-methyl-4-N-n-propyl-N-phenylmercaptoethylaminobenzaldehyde, 2-methyl-4-N-n-butyl-N-phenylmercaptoethylaminobenzaldehyde, 2-methyl-4-N-ethyl-N-(2'-benzthiazolyl)-mercaptoethylaminobenzaldehyde and 2-methyl-4-N,N-bis-(phenylmercaptoethyl)-aminobenzaldehyde.

Condensation of the aldehydes of the formula (2) with the cyano compound of the formula

is advantageously carried out with the application of heat in the presence of a basic catalyst, for example, ammonia, dimethylamine, diethylamine, piperidine, piperidine acetate, sodium or potassium alcoholate, if necessary, in the presence of a solvent, for example, methanol, ethanol, benzene, toluene, xylene, chloroform or carbon tetrachloride. When using solvents, the water formed during the reaction can be removed continuously from the reaction mixture by azeotropic distillation of the solvent, whereby the reaction equilibrium is shifted constantly in favour of the condensation product. Condensation may also be effected without a basic catalyst in glacial acetic acid or in some other organic acid, or in the absence of a solvent by fusing the reactants together in the presence of a basic catalyst, for example, ammonium acetate or piperidine acetate.

The aldehydes can be replaced by the aldimines thereof, that is to say, the condensation products obtained with primary amines, especially aminobenzenes, in other words, the so-called Schiff's bases of the formula

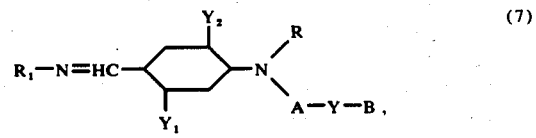

in which $R_1$ preferably represents a benzene residue, for example, a phenyl or sulphophenyl residue. The compounds of the formula (7) may be obtained by condensing the product obtained by reacting formaldehyde and a compound of the formula

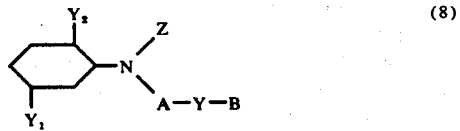

with a nitrobenzene, for example, a nitrobenzenesulphonic acid in the presence of iron and hydrochloric acid in accordance with Example 17 of U.S. Pat. No. 2,583,551.

In process (b) of the invention, the starting materials used are advantageously compounds of the formula

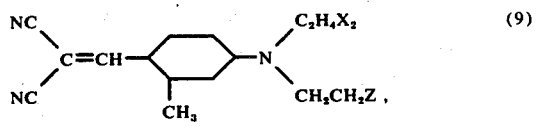

in which $X_2$ represents a hydrogen or a halogen atom and Z represents a halogen atom or an arylsulphonyloxy group.

These are condensed, for example, with the following mercaptans: phenylmercaptan, 2-, 3- or 4-chlorophenylmercaptan, 2,4- or 2,5-dichlorophenylmercaptan, 2-, 3- or 4-methylphenylmercaptan, 2,4- or 2,5-dimethylphenylmercaptan, 2-, 3- or 4-methoxyphenylmercaptan, 2,4- or 2,5-dimethoxyphenylmercaptan, 2- or 4-nitrophenylmercaptan, 2- or 4-carbomethoxyphenylmercaptan, 2-mercaptobenzthiazole, 2-mercapto-6-chlorobenzthiazole, 2-mercapto-4-chlorobenzthiazole, 2-mercapto-4-methylbenzthiazole, 2-mercapto-6-methylbenzthiazole, 2-mercapto-6-methoxybenzthiazole, 2-mercapto-6-ethoxybenzthiazole, 2-mercaptobenzoxazole and 2-mercaptobenzimidazole.

The reaction with the arylmercaptan is advantageously carried out in an organic solvent, preferably an alcohol, in the presence of an alkali metal hydroxide, an alkali metal alcoholate or an alkali metal carbonate at an elevated temperature, advantageously at the boiling temperature of the alcohol. It is advantageous to use at least one mol of the alkali metal hydroxide or alkali metal carbonate for each mol of the halogen compound.

The new dyestuffs, which have a high melting points, are suitable for dyeing and printing man-made fibres, for example, cellulose acetate fibres, but especially aromatic polyester fibres, particularly after the dyestuffs have been converted into a state of fine division, for example, by grinding, pasting, reprecipitation and so forth. They produce pure, strong, greenish yellow dyeings possessing excellent fastness to light and sublimation on the said fibres by the conventional dyeing processes, for example, when applied in a dyebath containing a fine dispersion of dyestuff and advantageously a dispersing agent at a temperature close to 100° C, if necessary, in the presence of a swelling agent, or at a temperature above 100° C under superatmospheric pressure. The new dyestuffs also have the advantage that they only very slightly stain wool and other fibres that may be present in the dyebath. They are therefore very suitable for dyeing union fabrics made from a mixture of polyester fibre and wool or, for example, a mixture of polyester fibre and cellulose triacetate. They may also be used for spin-colouration in bulk.

The dyestuffs of the invention are also suitable for application by the so-called Thermosol process in which the fabric to be dyed is impregnated at a temperature preferably not exceeding 60° C with an aqueous dispersion of the dyestuff which advantageously contains 1 to 50% of urea and a thickening agent, especially sodium alginate and is then squeezed in the usual manner, advantageously so as to retain 50 to 100% of dye-liquor, based on the dry weight of the goods. To fix the dyestuff, the material so impregnated is heated to a temperature above 100° C, for example, to a temperature between 180° and 210° C, advantageously after drying, for example, in a current of warm air.

The Thermosol process described above is specially suitable for the dyeing of union fabrics made from polyester and cellulosic fibres, especially cotton. When used for this purpose, the padding liquor may contain dyestuffs suitable for dyeing cotton, for example, vat dyestuffs, in addition to the dyestuffs of the invention. When vat dyestuffs are used, the padded fabric must be treated with an aqueous alkaline solution of one of the reducing agents customarily used in vat dyeing subsequent to the heat treatment. The dyeings and prints obtained possess good properties of general fastness and, in particular, display good fastness to light and sublimation.

The following Examples illustrate the invention. Unless otherwise stated, the parts and percentages are by weight.

EXAMPLE 1

39.5 Parts of N-ethyl-N-(β-chloroethyl)-m-toluidine and 39.4 parts of 2,5-dichlorothiophenol are boiled for 4 hours under reflux in a solution containing 4.6 parts of sodium in 100 parts by volume of absolute alcohol.

The sodium chloride which forms is removed by filtration and the filtrate is evaporated. The N-ethyl-N-(2',5'-dichlorophenylmercapto)-ethyl-m-toluidine which remains is distilled. It boils at 153° to 159° C under a pressure of 0.02 mm Hg.

13.6 Parts of the compound so obtained are introduced at 15° C into a mixture of 11.1 parts by volume of dimethylformamide and 9.4 parts by volume of phosphorus oxychloride and the batch is stirred for 5 hours at 60° C. It is discharged on to ice, chloroform is added, the mixture of ice and chloroform is neutralized with sodium hydroxide solution, the chloroform phase is washed with water, dried with sodium sulphate and evaporated. The aldehyde of the formula

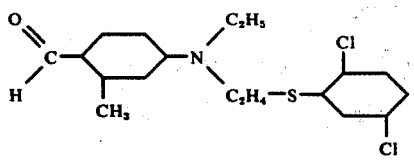

is obtained in the form of an oil. 7.4 Parts of the aldehyde together with 1.5 parts of malonic acid dinitrile and 0.2 part by volume of piperidine are boiled for 4 hours under reflux in 70 parts by volume of absolute ethanol, whereby a yellowish orange precipitate soon forms. After cooling the batch to room temperature, the dyestuff of the formula

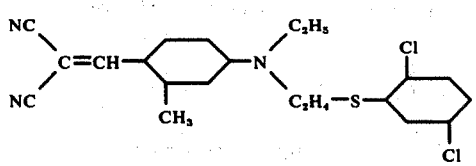

is isolated by suction filtration, washed with ethanol (about 95%) and dried in a vacuum cabinet. It melts at 139° to 140° C.

In the following Table is listed a series of further dyestuffs of the formula

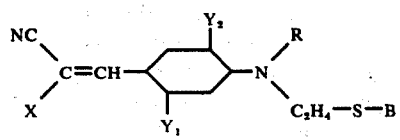

which may be obtained by the process described in this Example and which also dye polyester fibres pure, greenish yellow shades possessing excellent fastness to light and sublimation.

| | B | R | $Y_1$ | $Y_2$ | X |
|---|---|---|---|---|---|
| 1 | 4-chlorophenyl | ethyl | methyl | H | cyano |
| 2 | 2,5-dichlorophenyl | ethyl | methyl | H | carbethoxy |
| 3 | 2,5-dichlorophenyl | ethyl | methyl | H | phenylsulphonyl |
| 4 | 2-benzthiazolyl | ethyl | methyl | H | cyano |
| 5 | 2,5-dichlorophenyl | cyanoethyl | H | H | cyano |
| 6 | 2,5-dichlorophenyl | benzyl | H | H | cyano |
| 7 | 3,4-dichlorophenyl | ethyl | methyl | H | cyano |
| 8 | 2,5-dichlorophenyl | ethyl | methoxy | H | cyano |
| 9 | 2,5-dichlorophenyl | ethyl | methyl | methyl | cyano |
| 10 | 3,5-dichlorophenyl | ethyl | methyl | methyl | cyano |
| 11 | 2,4-dichloro-5-methylphenyl | ethyl | methyl | H | cyano |
| 12 | 2,5-dichlorophenyl | n-butyl | H | methoxy | cyano |
| 13 | 4-bromophenyl | ethyl | methyl | H | cyano |

EXAMPLE 2

5.5 Parts of the dyestuff of the formula

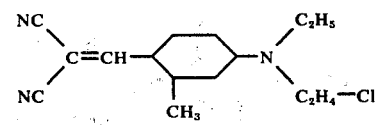

and 4.3 parts of 2,5-dichlorothiophenol are boiled for 3 hours under reflux in a solution containing 0.46 part of sodium in 100 parts by volume of absolute alcohol. The hot solution is separated from the sodium chloride which forms by filtration. The dyestuff crystallizes from the filtrate in the form of an orange powder melting at 136° to 138° C. It is identical with the dyestuff obtained by the process described in Example 1.

EXAMPLE 3

46.4 Parts of N,N-bis-(β-chloroethyl)-meta-toluidine and 63.6 parts of 4-chlorothiophenol are boiled for 4 hours under reflux in a solution containing 9.2 parts of sodium in 100 parts by volume of absolute alcohol. The sodium chloride which forms is removed by filtration, the filtrate is evaporated, the residue is dissolved in chloroform, washed and dried with calcium chloride. A pale yellow oil remains which eventually solidifies to white crystals. When recrystallized once from petroleum ether, the N,N-bis-(β-para-chlorophenylmercaptoethyl)-meta-toluidine melts at 72° to 76° C. 13.5 Parts of this compound are introduced at 15° to 20° C into a mixture of 5.6 parts by volume of dimethylformamide and 4.7 parts by volume of phosphorus oxychloride, and the batch is stirred for 5 hours at 60° C. It is then discharged on to ice, chloroform is added and the mixture is neutralized with sodium hydroxide solution. The chloroform phase is washed with water, dried with sodium sulphate and evaporated. 14.4 Parts of a yellowish oil remain which solidifies to a white cake of crystals.

The crude aldehyde of the formula

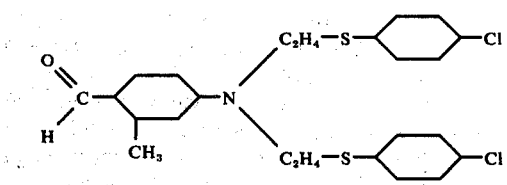

melts at 80° to 85° C.

4.8 Parts of the aldehyde so obtained are boiled for 4 hours under reflux together with 0.7 parts of malodinitrile and 0.1 part by volume of piperidine in 20 parts by volume of absolute ethanol. After cooling to room temperature, the orange dyestuff of the formula

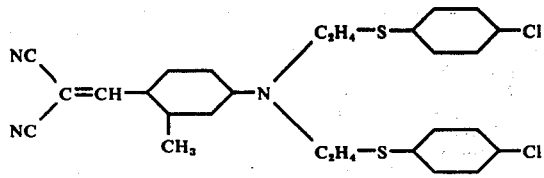

is isolated by suction filtration, washed with a small amount of 95% ethanol and then dried in a vacuum cabinet. It melts at 130° to 132° C.

In the following Table is listed a series of further dyestuffs of the formula

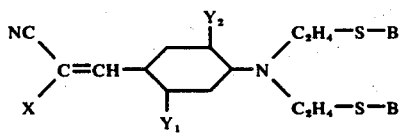

which may be obtained by the process described in this Example and which dye polyester fibres pure, greenish yellow shades possessing excellent fastness to light and sublimation.

| | B | $Y_1$ | $Y_2$ | X |
|---|---|---|---|---|
| 1 | 2,5-dichlorophenyl | methyl | H | cyano |
| 2 | 3,5-dichlorophenyl | methyl | H | cyano |
| 3 | 3,4-dichlorophenyl | methyl | H | cyano |
| 4 | 4-bromophenyl | methyl | H | cyano |
| 5 | 2,5-dichlorophenyl | H | H | carbethoxy |
| 6 | 2,5-dichlorophenyl | methoxy | H | cyano |
| 7 | 3,4-dichlorophenyl | chlorine | H | cyano |
| 8 | 2,5-dichlorophenyl | methyl | methyl | cyano |
| 9 | 4-chlorophenyl | methyl | H | phenylsulphonyl |

EXAMPLE 4

A dyestuff identical with dyestuff No. 1 of the Table in Example 3 may be obtained when 1 mol of the dyestuff of the formula

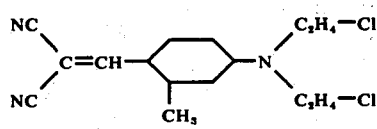

is treated with 2 mols of 3,5-dichlorothiophenol in the manner described in Example 2. It melts at 147° to 148° C.

Analysis: Cl calculated: 23.90; Cl found: 23.80; S calculated: 10.81; S found: 10.60.

EXAMPLE 5

200 Parts of epichlorohydrin are added at 15° to 20° C to a mixture of 270 parts of N-ethyl-meta-toluidine in 200 parts of water and 300 parts by volume of glacial acetic acid and the batch is stirred for 3 hours at 10° to 20° C. The readily volatile components are then distilled at a maximum temperature of 75° C and finally in a high vacuum. 505 Parts of an oil of the formula

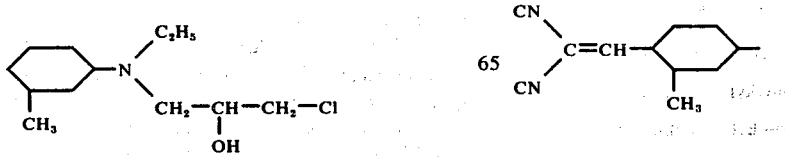

remain. 4.6 Parts of sodium are dissolved in 200 parts by volume of absolute alcohol, 39.4 parts of 2,5-dichlorothiophenol are added and then a solution of 45.6 parts of the amine described above in 100 parts by volume of absolute alcohol is added while stirring and boiling under reflux. After stirring and boiling under reflux for 4 hours, the batch is cooled to room temperature, freed from sodium chloride by filtration, dissolved in benzene, washed successively with sodium carbonate solution and water, dried with sodium sulphate and concentrated. The residue is distilled in a high vacuum. 50 Parts of the amine of the formula

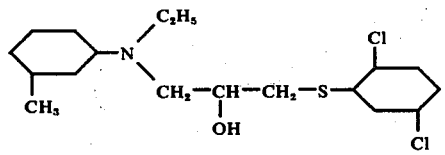

are obtained at 185° to 198° C under a pressure of 0.02 mm Hg.

26.3 Parts of this amine are boiled for 3 hours under reflux in 100 parts by volume of acetic anhydride, concentrated, the residue is dissolved in chloroform, washed neutral with water, dried with sodium sulphate, filtered and concentrated. 28.3 Parts of a brown oil remain which distils in a high vacuum at 183° to 186° C 0.015 mm Hg. It corresponds to the formula

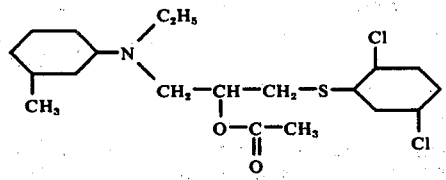

17.2 Parts of this amine are dissolved in 12.5 parts by volume of dimethylformamide and 4.4 parts by volume of phosphorus oxychloride are added dropwise at 15° to 20° C. The batch is then stirred for 1 hour at 95° C, discharged on to ice and stirred for some time. The hard mass which forms is treated with a 10% sodium carbonate solution and suction filtered. 14 Parts of the aldehyde of the formula

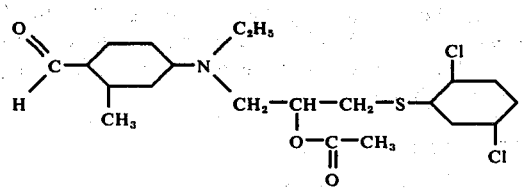

remain. This is condensed with 2.2 parts of malodinitrile in methanol in the usual manner and the dyestuff of the formula -continued

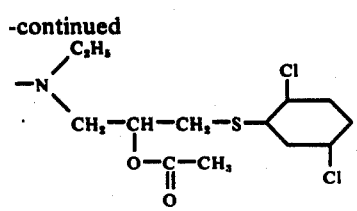

is obtained.

It dyes cellulose acetate and polyester materials greenish yellow shades possessing good properties of fastness.

EXAMPLE 6

When esterification is carried out with benzoyl chloride instead of acetic anhydride and the procedure described in Example 5 is followed, the dyestuff of the formula

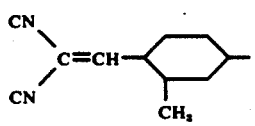

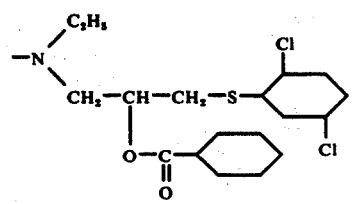

is obtained which dyes hydrophobic materials, especially polyester fibres and fabrics, greenish yellow shades possessing excellent properties of fastness.

EXAMPLE 7

1 Part of the dyestuff of the formula

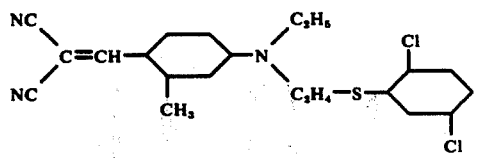

is ground wet with 2 parts of a 50% aqueous solution of sulphite cellulose waste liquor and the batch is dried.

The dyestuff preparation so obtained is mixed with 40 parts of a 10% aqueous solution of a condensation product obtained from octadecyl alcohol and 20 mols of ethylene oxide and then 4 parts of a 40% acetic acid solution are added. A dyebath of 4,000 parts is prepared therefrom by dilution with water.

100 Parts of cleaned polyester fibre material are entered into this dyebath at 50° C, the temperature is raised to 120° to 130° C within 30 minutes and dyeing is carried out for one hour at that temperature in a closed vessel. The material is then well rinsed. A greenish yellow dyeing possessing excellent fastness to light and sublimation is obtained.

EXAMPLE 8

A mixture is prepared from
300 parts of gum arabic (1:1)
300 parts of crystal gum (1:2)
250 parts of water
40 parts of cyclohexane
40 parts of thiodiglycol
50 parts of a 10% solution of the sodium salt of meta-nitrobenzene-sulphonic acid
20 parts of a mixture of potassium oleate and pine oil
1,000 parts.

200 Parts of the dyestuff preparation obtained in the manner described in Example 1 are stirred into 800 parts of the stock thickening so prepared by means of a high-speed stirrer until dispersion is complete. A polyethylene terephthalate fabric is printed with this paste. After printing, the fabric is dried, steamed for 45 minutes at ¾ atmosphere (gauge), rinsed for 10 minutes in cold water, centrifuged and dried. A fast, greenish yellow print is obtained.

EXAMPLE 9

4.6 Parts sodium metal were dissolved in 100 vol-parts dry ethanol. The mixture was treated with 36.7 parts N,β-chloroethyl-N-ethyl-aniline and 36.8 parts 2-mercapto-benzothiazole, refluxed 20 hours and filtered while hot. The filtered solution was evaporated in vacuo and the residue was dissolved in chloroforme, washed with water until neutral, dried over sodium sulfate and evaporated in vacuo. The residue was formylated according to Vilsmeyer and the resulting aldehyde was condensed with malodinitrile to give a dyestuff of the formula

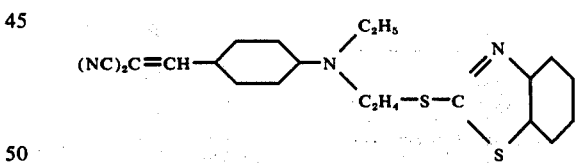

which dyes polyester fibers in a greenish yellow shade. In a strictly analogous way the following dyestuffs were prepared which dye polyester fibers in yellow shades

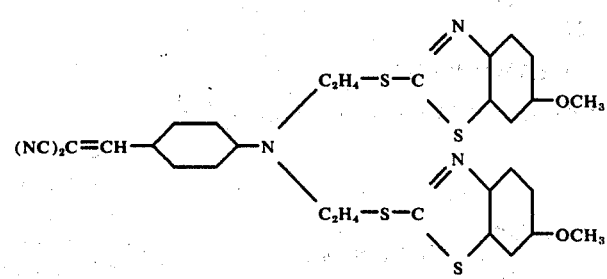

1

-continued

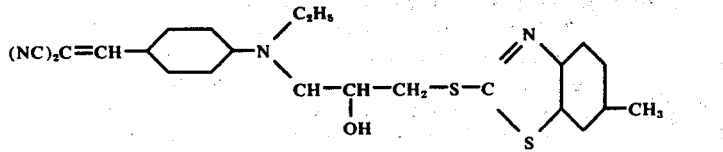

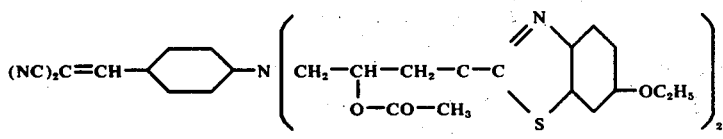

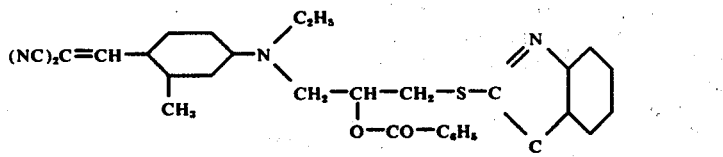

were prepared.

| | B | Y₁ | Y₂ | X |
|---|---|---|---|---|
| 1 | 2-Mercapto-benzothiazole | Methyl | H | Cyano |
| 2 | 2-Mercapto-benzoxazole | " | H | " |
| 3 | 2-Mercapto-benzoimidazole | Chlorine | H | " |
| 4 | 2-Mercapto-quinoline | H | Methyl | " |
| 5 | 2-Mercapto-pyridine | Methoxy | H | Carboethoxy |
| 6 | 2-Mercapto-pyrimidine | Chlorine | H | Phenylsulphonyl |
| 7 | 2-Mercapto-thiazoline | " | H | Cyano |
| 8 | 2-Mercapto-1,2,4-triazole | H | Methyl | " |
| 9 | 2-Mercapto-4-methyl-triazole-2-carboxylic acid methyl ester | H | H | " |

EXAMPLE 10

In the same way as in Example 9 the dyestuffs of the formula

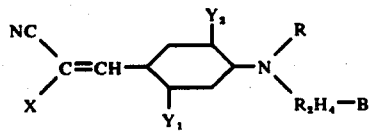

were prepared.

| | B | R | Y₁ | Y₂ | X |
|---|---|---|---|---|---|
| 5 | 2-Mercapto-benzothiazole | β-Cyanoethyl | Methyl | H | Cyano |
| 6 | 2-Mercapto-benzoxazole | Ethyl | Methyl | H | Carbethoxy |
| 7 | 2-Mercapto-benzimidazole | β-Butoxyethyl | H | H | Phenylsulphonyl |
| 8 | 2-Mercapto-quinoline | β-Phenylethyl | Methyl | Methyl | Cyano |
| 9 | 2-Mercapto-1-methyl-imidazol | Benzyl | Methoxy | " | " |
| 10 | 2-Mercaptopyrimidine | n-Butyl | " | H | " |
| 11 | 2-Mercaptopyrimidine | Ethyl | " | H | " |
| 12 | 2-Mercapto-thiazoline | β-Cyanoethyl | Methyl | H | Carboethoxy |
| 13 | 2-Mercapto-1,2,4-triazole | Ethyl | H | Methoxy | Cyano |
| 14 | 2-Mercapto-4-methyl-thiazole-5-carboxylic acid ethyl ester | β-Methoxyethyl | Methyl | H | " |

The dyestuffs dye polyester fibers in greenish yellow shades were prepared.

EXAMPLE 11

In the same way as in Example 3 dyestuffs of the formula

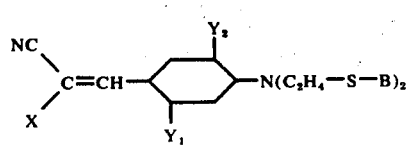

The dyestuffs dye polyester fibers in greenish yellow shades.

What we claim is:

1. A water insoluble styryl dyestuff of the formula

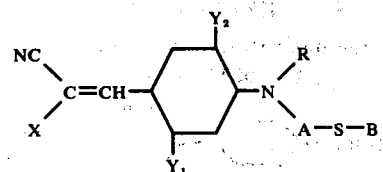

in which X represents a cyano, carbalkoxy containing up to 3 carbon atoms or phenylsulphone group, Y₁ and Y₂ each represents a hydrogen atom, methyl or methoxy group, R represents $C_1$ to $C_4$ alkyl, phenylalkyl containing up to 8 carbon atoms, cyanoethyl, alkoxyalkyl containing up to 6 carbon atoms, or fatty acid acyloxyalkyl group up to 3 carbon atoms, or a radical of the formula —A—S—B, and A represents alkylene group containing up to 3 carbon atoms that may be substituted by a fatty acid acyloxy containing up to 2 carbon atoms or a benzoyloxy group and B represents either a benzthiazolyl radical which may be substituted by chlorine, methyl, methoxy, ethoxy or a benzoxazolyl-2- or benzoimidazolyl-2.

2. A dyestuff according to claim 1, of the formula

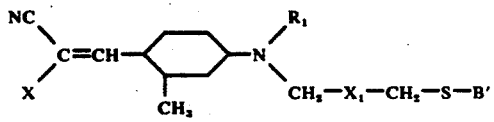

in which X represents a cyano, carbalkoxy containing up to 3 carbon atoms or phenylsulphone group, B' represents benzthiazolyl, which may be substituted by chlorine, methyl, methoxy or ethoxy, $X_1$ is a direct bond or a group of the formula

in which $R_2$ is methyl or phenyl and $R_1$ is $C_1$-$C_4$-alkyl or a radical of the formula —$CH_2CH_2$—S—B'.

3. The dyestuff claimed in claim 1 of the formula

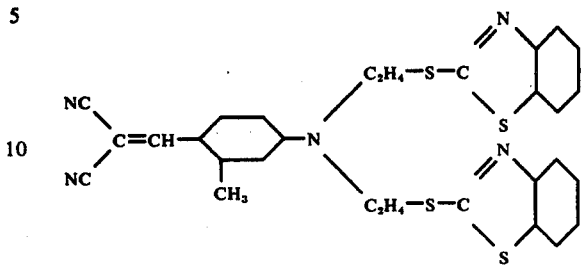

4.

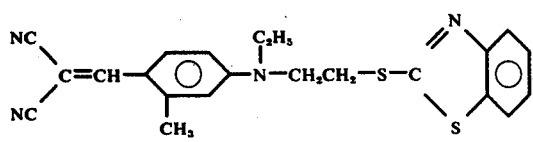

* * * * *